(12) United States Patent
Viswanathan

(10) Patent No.: US 6,727,389 B1
(45) Date of Patent: Apr. 27, 2004

(54) CYCLIC ORGANO-OXIDE STORAGE VENT SCRUBBING

(75) Inventor: Krishnan Viswanathan, Houston, TX (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 10/417,287

(22) Filed: Apr. 16, 2003

(51) Int. Cl.[7] ..................... C07C 213/04; C07C 213/10; C07D 301/32
(52) U.S. Cl. .................. 564/477; 564/475; 549/538; 549/541; 549/542
(58) Field of Search ................... 564/477, 475; 549/538, 541, 542

(56) References Cited

U.S. PATENT DOCUMENTS 4,355,181 A * 10/1982 Willis et al. ................ 564/477

* cited by examiner

Primary Examiner—Ba K. Trinh
(74) Attorney, Agent, or Firm—Roderick W. MacDonald

(57) ABSTRACT

A method for processing at least one cyclic organo-oxide using a closed loop scrubber/holding tank system that contains at least one amine, and circulating the amine through the closed loop while admitting the cyclic organo-oxide to the closed loop.

11 Claims, 3 Drawing Sheets

FIG. 1 EO Process, Prior Art

FIG. 2 Purified EO Tank Farm Storage, Prior Art

CYCLIC ORGANO-OXIDE STORAGE VENT SCRUBBING

BACKGROUND OF THE INVENTION

1. Field of the Invention

This invention relates to the recovery of cyclic organo-oxide vapors from storage units for same. For example, this invention relates to recovering ethylene oxide vapors from storage tanks associated with an ethylene oxide plant, particularly when such plant or a significant part thereof is shut down for maintenance purposes.

2. Description of the Prior Art

For sake of clarity and brevity, this invention will be described in detail in respect of ethylene oxide production, but it should be understood that this invention is broadly applicable to cyclic organo-oxides such as propylene oxide that are susceptible to dissolution in amines as described hereinafter with respect to ethylene oxide.

In a conventional ethylene oxide production plant, ethylene and oxygen are reacted at an elevated temperature of from about 500° F. to about 550° F. under slight pressure in the presence of a catalyst to form ethylene oxide (EO). The reaction is fast, on the order of about 1 second and high yielding, approaching 90%. The EO reaction product is normally gaseous and contains newly formed EO, unreacted ethylene, and various by-products but mainly carbon dioxide.

The EO is separated from the ethylene and by-products in a water-wash column (EO scrubber) in the manner of a solvent recovery process. The EO is absorbed by the water, and the ethylene and by-products are not. The EO/water solution is then steam stripped and purified by fractionation. The by-products and ethylene are split with the ethylene being recycled to the reactor that forms EO aforesaid, and the carbon dioxide, etc., being separately recovered for other uses. This process yields about 1.4 pounds of EO per pound of ethylene feed at high yields, e.g., about 89%.

EO as a liquid boils at about 56° F. to form a colorless gas at room temperature. It is traded commercially as a high purity technical grade, e.g., 99.7% purity. Because of its volatility under normal conditions, care must be given in its storage and transportation to keep it out of the ambient atmosphere.

EO is an intermediary chemical useful for making a number of derivatives of commercial value. The predominant derivative is ethylene glycol or EG (sometimes called monoethylene glycol or MEG to distinguish it from diethylene glycol or DEG, and triethylene glycol or TEG). Other derivatives include ethoxylates used in biodegradable detergents, paint solvents, and the textile industry.

Often an EO production plant will have associated with it a glycol production unit for converting EO into EG (MEG). In an EG plant an EO/water mixture from the EO stripper, or purified EO from the purification unit, or both are fed to an EG reactor at a pressure of from about 200 psig to about 600 psig wherein essentially all of the EO is converted to EG, plus minor amounts of DEG and TEG. Water is kept in an excess to assure high EG selectivity. EG yield is normally quantitative. The EG/water product is then subjected to a concentration step to remove excess water, and then to a series of fractionators to remove the EG, DEG, and TEG components separately from one another. EG is used in making automotive antifreeze, polyethylene terephthalate, and other polyester polymers. DEG and TEG are useful as solvents and drying agents for refinery gases.

Pure EO product from the EO plant is normally sent to storage, e.g., in a tank farm composed of a plurality of individual storage tanks that, at a given moment, are in various stages from empty to filling with EO to full of EO. EO vapors from these tanks are not vented to the atmosphere, but rather are routinely sent to what is known as a tank farm vent scrubber (TFVS). In a conventional TFVS, the normally gaseous EO received from the tanks in the tank farm is contacted with water in a manner such that all the EO is dissolved in the water. TFVS units operate at ambient temperature and a slight overpressure using internal packing for thorough mixing of the EO and the water to assure complete absorption of the EO into the water passing through the TFVS unit. The EO/water solution from the TFVS unit is returned to the EO production process, e.g., the EG formation reactor. This way all vaporous EO recovered from the tank farm is, by way of the TFVS, returned to the EO/EG process for recovery.

From time to time various units in the EO/EG process need to be shut down for routine maintenance and the like. This is called "turnaround." For example, the EG formation unit is shut down for turnaround every 1.5 to 2 years. Such a turnaround can take several weeks time. During this time, the TFVS unit can still be receiving EO vapor from the tank farm and/or an associated EO derivatives unit that makes ethers and the like. The EO/water product of such TFVS unit must continue to be processed even though that product cannot, for the time period of the turnaround, be returned to the EO process during turnaround.

Heretofore, during a turnaround, the TFVS EO/water product has been processed by adding sulfuric acid to the product as a catalyst for the reaction of EO with water to form EG. The mixture of EO, water, and sulfuric acid was passed to at least one temporary holding tank for at least a two-hour residence time to allow the EO to be transformed primarily into EG plus minor amounts of DEG and TEG, after which the sulfuric acid was neutralized and separately processed for the recovery of EG, DEG, and TEG.

This prior art practice has several deficiencies. Since the apparatus and procedure was used infrequently, problems arose in operating the temporary equipment set up due to unfamiliarity and lack of practice in operating. The temporary equipment, if made from carbon steel was subject to significant corrosion consequences, and to make the equipment from stainless steel was prohibitively expensive.

Other options to the sulfuric acid approach, such as shutting down the associated EO derivatives unit or passing the EO/water product through a resin or zeolite bed, were also unduly expensive.

The substitution of the sulfuric acid catalyst with an alkali such sodium hydroxide to absorb and react with the EO proved not to be viable because the caustic catalyzed reaction was a hundred times slower than the already slow sulfuric acid catalyzed reaction.

Ammonia could be used to keep EO out of the ambient atmosphere but this is just putting nitrogen into the atmosphere in lieu of EO which is not environmentally desirable.

Accordingly, it is highly desirable to have a process for processing TFVS EO/water product on at least a temporary basis that is cost effective, fast reacting with EO, does not require expensive materials such as stainless steel, is uncomplicated in its operation, and is environmentally friendly. The answer is the instant invention.

SUMMARY OF THE INVENTION

In accordance with this invention a cyclic organo-oxide is recovered by employing at least one of a primary amine and a primary amino alcohol in the manner described hereinbelow.

Primary amines and amino alcohols react quickly with cyclic organo-oxides, are not corrosive like sulfuric acid, are inexpensive, and form reaction products that have commercial value. In addition such amines are easy to work with safely and environmentally friendly due to their low vapor pressure and relative inflammability. For example, monoethanolamine (MEA) has a very low vapor pressure (0.1 of an atmosphere at 68° F.) and is essentially not flammable (196° F. flash point) under normal conditions.

Further, primary amines such as monoethanolamine can be mixed with water to ensure that the absorption fluid does not become too viscous and to lower the freezing point of the amine. This beneficial effect is very useful in many applications of this invention where water is a prevalent material such as in an EO plant.

DETAILED DESCRIPTION OF THE INVENTION

Figure 1:
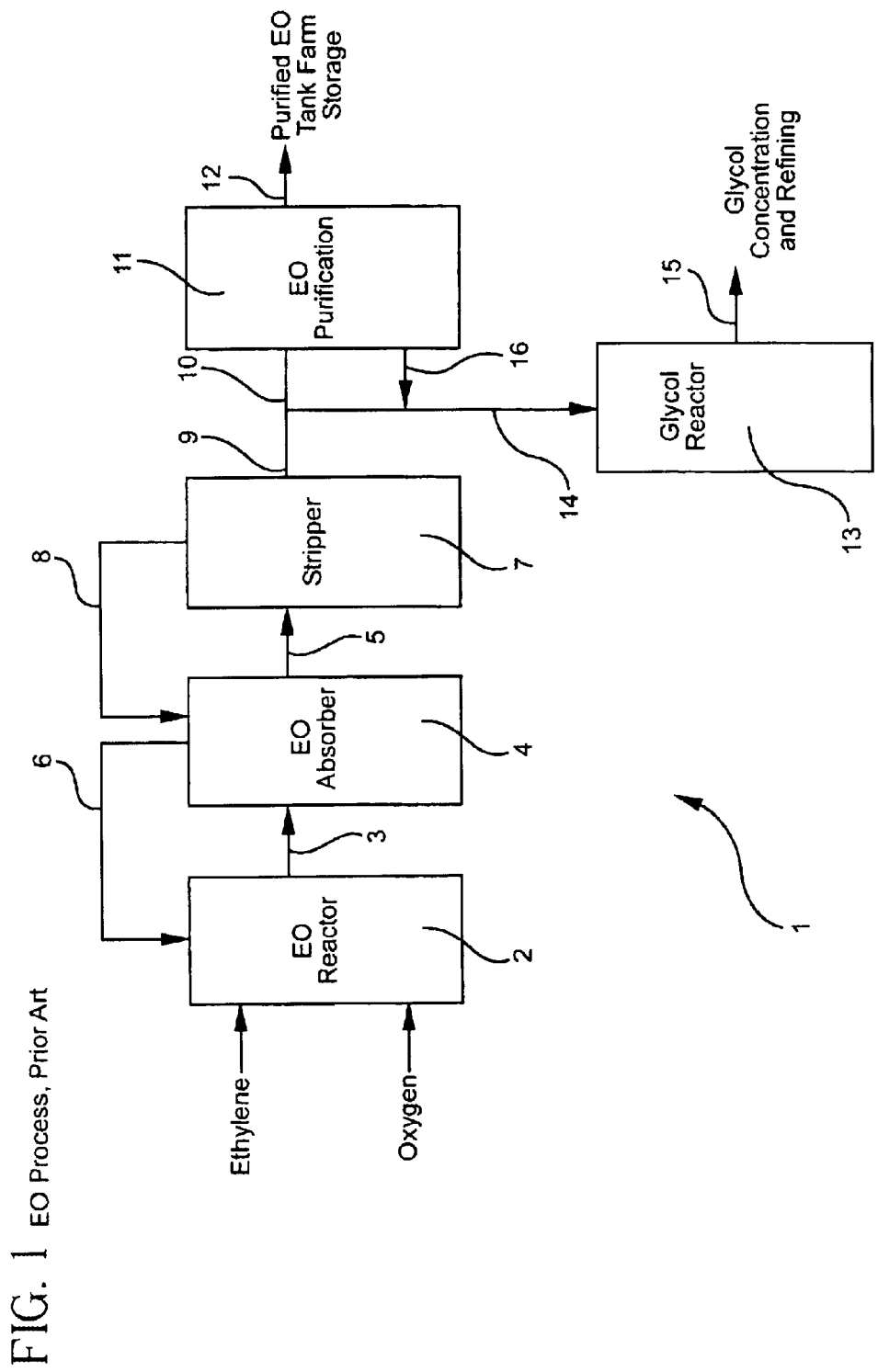
FIG. 1 shows a block diagram of a conventional plant for the production of EO.

FIG. 1 shows a typical EO production plant 1 wherein ethylene and oxygen are reacted in an EO reactor 2 in the manner described hereinabove to form EO. The normally gaseous reaction product stream 3 is composed of EO, unreacted ethylene, and by-product (mainly carbon dioxide) is removed from reactor 1 and is passed into EO absorber 4 wherein an EO/water product stream 5 is formed and separated from the unreacted ethylene and by-product stream 6. Carbon dioxide can be separated from stream 6 after compression of same followed by carbon dioxide removal (not shown), after which the remaining unreacted ethylene and by products in stream 6 are returned as co-feed to reaction zone 2.

Absorber 4 is a water wash scrubber that operates like a solvent extractor by absorbing (dissolving) EO out of stream 3 to form an EO/water stream 5.

The EO/water product stream 5 of absorber (scrubber) 4 is a water stream containing from about 3% to about 5 weight (wt.) percent EO dissolved therein. Stream 5 is passed to stripper 7 wherein stream 5 is steam stripped to remove water there from which water can be returned by way of line 8 to absorber 4 to remove additional EO from incoming line 3, and to produce a new EO/water stream 9 that is more concentrated in EO than was stream 5.

Stream 9 can, for example, be composed of a 50/50 weight mixture of EO dissolved in water. This type of stream is useful in more than one way. It can be sent by way of line 10 to EO purification unit 11 wherein by fractionation an essentially pure EO stream is formed and recovered by way of line 12.

Stream 9 can also be sent to a glycol production unit 13 by way of line 14 wherein EO is reacted with water in the manner described hereinabove to form a glycol product containing EG and minor amounts of DEG and TEG. This glycol product is removed by way of line 15 for further processing such as forming a crude glycol concentrate which is subsequently processed in a glycol refinery for the recovery of separate EG, DEG, and TEG product streams.

An EO/water mixture left over from the EO purification process 11 can be passed by way of line 16 to the glycol reaction unit 13 for the formation of additional glycol product.

Figure 2:
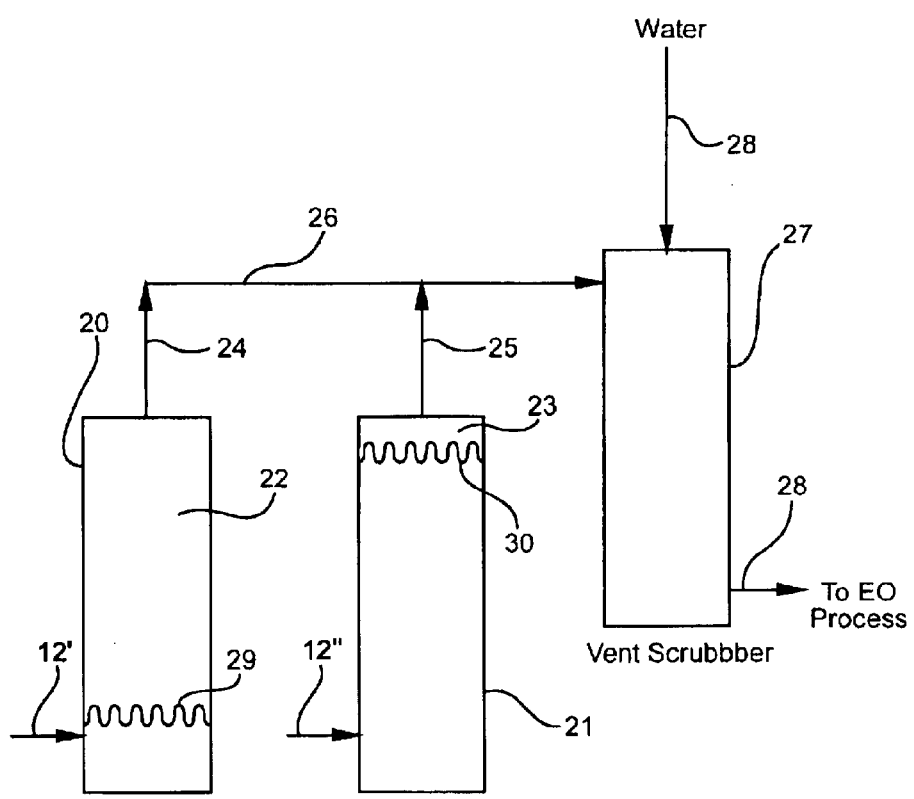
FIG. 2 shows a conventional TFVS in use in an EO Storage tank farm.

FIG. 2 shows a conventional tank farm wherein storage tanks 20 and 21 represent a plurality of such tanks all of which have their overhead vapors 22 and 23 functionally connected by overhead vent pipes 24 and 25 to manifold conduit 26 for transport of such vapors to a common TFVS 27. In scrubber 27 water from line 28 contacts EO vapor and absorbs same so that the product of scrubber 27 is an EO/water stream 28. Stream 28 is normally returned to the EO process of FIG. 1, e.g., to glycol reactor unit 13.

Tanks 20 and 21 are filled with liquid EO by way of branch lines 12' and 12" of line 12 of FIG. 1. When, for example, tank 20 is being filled with liquid EO passing from the interior of line 12' to the interior of tank 20 the EO liquid level 29 rises toward the top of tank 20, and as it rises it pushes EO vapor in the interior of tank 20 into line 24 and line 26 to the interior of TFVS 27 for dissolution into water flowing therein. By the time liquid level 29 has reached the full level shown by liquid level 30 in tank 21 a substantial amount of EO vapor has been passed into TFVS 27 and a substantial amount of EO/water solution 28 has been formed that must go somewhere. That "somewhere" in the prior art was a carbon steel tank which contained sulfuric acid catalyst for the conversion of the EO to EG and the attendant problems all as aforesaid.

Figure 3:
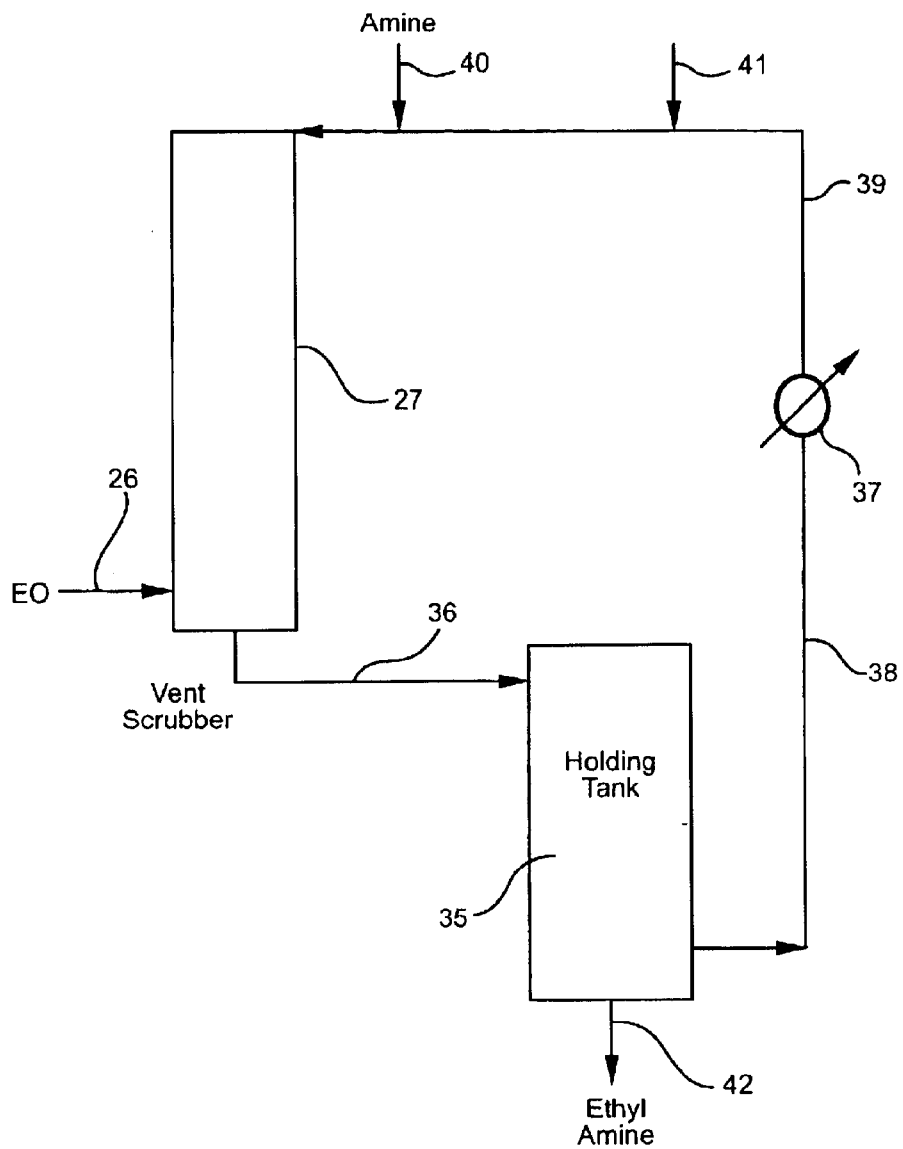
FIG. 3 shows apparatus embodying one particular application of the process of this invention.

By this invention, as shown in FIG. 3, the prior art process of temporary processing using sulfuric acid and its problems is replaced by a closed loop system comprising existing TFVS 27 in fluid connection with holding tank 35 by way of line 36. Tank 35 is in turn in fluid communication with heat exchanger 37 by way of line 38, and then by way of line 39 back to the interior of TFVS 27. At least one amine is introduced into this closed loop by way of line 40. Ethanolamine reaction product is removed from the closed loop by way of line 42 for further processing if desired. Alternatively, no reaction product need be removed from the loop during its operation throughout turnaround if the amine load initially in the loop was sufficient to take up all EO vapor introduced into scrubber 27 during the entire time length of the turnaround. This last alternative is attractive if tank 35 is portable, e.g., a truck trailer tank.

In the operation of this invention, EO flows into the interior of TFVS 27 wherein it is contacted with an amine 10 under conditions which promote the reaction of the EO with the amine to form an ethanolamine.

The cyclic organo oxide can be at least one with the formula

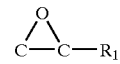

where $R_1$ is selected from the group consisting of hydrogen and a hydrocarbon having from 1 to 3, inclusive, carbon atoms. This includes ethylene oxide and propylene oxide.

The amine is at least one primary amine and/or primary amino alcohol having from 1 to 20, inclusive, carbon atoms per molecule. In the case of an EO plant where EO is conveniently available, the reaction of EO with ammonia in known manner readily produces monoethanolamine as an initial amine reactant in this invention. In this situation as additional EO enters scrubber 27 through line 26 it can either react with fresh monoethanolamine (MEA) to form diethanolamine (DEA) or even react with DEA to form triethanolamine (TEA). Thus, MEA in this process exhibits great capacity for taking up EO, and makes it plausible, for example, to take up EO during the entire length of turnaround without the need to add more MEA to the closed loop or to remove DEA or TEA reaction product from the loop. This is especially desirable when tank 35 is a portable tank, particularly a wheeled trailer tanker. Other amines react similarly in their take up of EO.

It should be noted that the invention operates, and operates well, without the use of a catalyst of any sort, a considerable material and operating advantage. It totally eliminates corrosive acidic catalysts without eliminating their function.

The amine reactant aforesaid can be employed in the loop by itself or in a carrier such as water. Water can be of value because it can depress the freezing point of some amines and/or ensure that the fluid circulating in the loop does not become unduly viscous. Up to a 50/50 weight ratio of amine to carrier can be employed.

This invention also has the advantage that it can generate net surplus heat. For example, the heat of reaction of EO with MEA is 1,070 BTU per pound of EO. Since this invention functions well at ambient temperatures, heat exchanger 37 can capture this excess heat for beneficial use elsewhere.

The reaction of this invention proceeds quickly, much more quickly than the prior art acid catalyzed process. For example, EO is completely consumed by MEA in a short time—22 minutes versus 2 hours for the prior art sulfuric acid catalyzed process. In this regard an experiment was conducted by mixing 105 grams (g.) of MEA with 6 milliliters of liquid EO at about 73.4° F. and the temperature of reaction continuously monitored. The amount of EO added was about 4.16 g., and with no heat loss, the expected final reaction temperature was 134.6° F. After 22 minutes of reaction time uncalibrated gas chromatographic analysis showed the EO remaining to be 0.0227%, DEA formed to be 10.5% and TEA formed to be 0.304%, all percent by weight. Based on the amount of EO used a 9% DEA yield could be expected which compares favorably with the 10.5% measured. Based on this, the conversion of EO was estimated to be 99.4% after 22 minutes.

A very important advantage for this invention is environmental friendliness in that an essentially quantative take up of cyclic organo oxide is common place, while the reaction product of this invention is a benign aqueous solution of useful amine compounds. For example, experiments were carried out wherein 100 g. of liquid MEA was added to 21 g. of liquid EO and left standing at room temperature for 30 minutes. The experiment was not carried out in a closed loop so some EO was lost to the atmosphere, but subsequent gas chromatographic analysis of the mixture showed no EO present. Rough calculation yields showed 16.4% EO equivalent (DEA and TEA) versus 15.3% added (excluding evaporated EO). This experiment was repeated two more times with similar results.

The amine reaction product, whether aqueous or not, has commercial value. In the case of EO, an aqueous solution of MEA, DEAT, and TEA can be processed in known manner to separately recover MEA (used in wood treating and carbon dioxide removal), DEA (used in pesticides and carbon dioxide removal) and TEA (used in cement grinding).

Because this invention is so amenable to temporary installations, it could be employed with a truck trailer as the holding tank which trailer carries its own self-contained pad, and thus leaves no footprint in the plant after turnaround is completed.

A liquid carrier for the amine reactant can be advantageous for reasons other than those set forth hereinabove. For example, a water carrier will absorb by itself 5 to 6 wt. % EO and thus compliments the solubility of say MEA for EO. Thus, although MEA has a solubility for EO that is two to three times that of water, water as a carrier by itself picks up a finite amount of EO. This helps the chances that a single load of amine in a closed loop system will suffice for an entire turnaround period without the necessity of using solely amine in the system, or having to add amine or to remove reaction product from the closed loop during the turnaround time period. The relative ratio of amine to water used in this invention can vary widely, but will generally be in the weight ratio range of amine/water of from almost 100% amine to about 25/75, preferably 85/15.

EXAMPLE

A conventional TFVS in operable connection with the tank storage farm of an EO production plant receives EO containing vapors from the tank farm, and scrubs the EO out of such vapors using counter current flow of a liquid water EO absorbent stream. The TFVS holds two 20 foot tall beds of packing to ensure complete mixing of the absorbent water and the EO containing vapors, and consequent absorption of all the EO present in the TFVS by the water. Water at the rate of 50,000 pounds per hour is introduced at the top of the TFVS. A similar volume of water containing EO dissolved therein is removed from the bottom of the TFVS and returned to the EG unit of the EO production plant. The TFVS operates at ambient outside temperature and about 10 psig internal pressure.

When the EG unit is shut down for normal maintenance turnaround for a period of about 3 weeks, the TFVS still receives EO bearing vapors due to is the continued operation of the EO derivatives unit of the EO production plant.

The continued operation of the TFVS during turnaround is at a reduced level of about 20,000 pounds per hour of liquid EO absorbent, i.e., reduced from the 50,000 pounds per hour of liquid water absorbent used during normal operation of the EO production plant, including its EG unit.

In accordance with this example, a closed loop between a temporary tank and the existing TFVS is established as described hereinabove and shown in FIG. 3. Fifty thousand pounds of an 85/15 weight mixture of MEA to liquid water is established in the closed loop and circulated through the TFVS at a rate of about 20,000 pounds per hour with the TFVS operating at ambient outdoor temperature and about 10 psig internal pressure.

The heat exchanger 37 in the closed loop is operated so as to remove the heat of reaction of the MEA and EO and keep the TFVS essentially at ambient outside temperature. Tank 35 provides, among other obvious functions, a residence time locale for the reaction of MEA with EO.

At the end of the turnaround the totality of the reaction product comprising water, unreacted MEA, DEA, and TEA is collected in the holding tank 35. The closed loop is disassembled and the TFVS put back onto its normal operation mode of 50,000 pounds of water per hour with the EO production plant at normal operating levels.

The contents of the holding tank are transferred to a separate facility for the recovery of the MEA, DEA, and TEA.

In this example, the existing circulating pump for the TFVS in normal operation is used to circulate the MEA/water mixture continually through the TFVS. A vapor equalization line is established between the TFVS and tank 35 with pressure relief protection set at 35 psig. Tank 35 and the closed loop piping are composed of carbon steel as is the TFVS. Less than 200 feet of new piping is required to establish the closed loop.

I claim:

1. A method for processing a cyclic organo-oxide comprising providing a scrubber, holding tank, and heat exchanger in a closed fluid communication circuit that contains at least one cyclic organo-oxide, introducing into said circuit at least one amine, establishing in said circuit reaction conditions of temperature and pressure that favor the reaction of said at least one amine with said cyclic organo-oxide to form an organo-amine, and recovering the organo-amine reaction product from said closed loop.

2. The method of claim 1 wherein said at least one amine is at least one of a primary amine and a primary amino alcohol having from 1 to 20, inclusive, carbon atoms per molecule.

3. The method of claim 1 wherein said cyclic organo-oxide is selected from the group consisting of

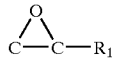

where $R_1$ is one of hydrogen, and a hydrocarbon having from 1 to 3, inclusive, carbon atoms.

4. The method of claim 3 wherein said cyclic organo-oxide is selected from the group consisting of ethylene oxide and propylene oxide.

5. The method of claim 1 wherein said cyclic organo-oxide is ethylene oxide and said amine is monoethanolamine.

6. The method of claim 1 wherein said cyclic organo-oxide is ethylene oxide, said scrubber is an ethylene oxide tank farm vent scrubber, and said holding tank is one of a permanent tank and a portable tank.

7. The method of claim 6 wherein said amine is at least one of a primary amine and primary amino alcohol having from 1 to 20, inclusive, carbon atoms per molecule.

8. The method of claim 7 wherein said amine is primary amino alcohol.

9. The method of claim 8 wherein said amine is monethanolamine.

10. The method of claim 1 wherein said closed circuit reaction conditions are a temperature of from about ambient to about 130° F. and a pressure above about 10 psig.

11. The method of claim 10 wherein said temperature is ambient and said pressure is above about 10 psig and below about 35 psig.

* * * * *